US007777072B2

(12) United States Patent
Ritter

(10) Patent No.: US 7,777,072 B2
(45) Date of Patent: *Aug. 17, 2010

(54) PROCESS FOR THE SYNTHESIS OF 2,5-DIHYDROXYTEREPHTHALIC ACID

(75) Inventor: Joachim C. Ritter, Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 122 days.

This patent is subject to a terminal disclaimer.

(21) Appl. No.: 12/041,960

(22) Filed: Mar. 4, 2008

(65) Prior Publication Data

US 2008/0161600 A1 Jul. 3, 2008

Related U.S. Application Data

(62) Division of application No. 11/604,935, filed on Nov. 28, 2006, now Pat. No. 7,345,194.

(51) Int. Cl.
*C07C 63/00* (2006.01)
(52) U.S. Cl. .......................... 562/405; 562/400; 562/412
(58) Field of Classification Search .................. 562/400, 562/405
See application file for complete search history.

(56) References Cited

U.S. PATENT DOCUMENTS

| | | | |
|---|---|---|---|
| 3,047,536 | A | 7/1962 | Gordon |
| 3,227,680 | A | 1/1966 | Tamblyn et al. |
| 3,894,079 | A | 7/1975 | Knobloch |
| 3,932,542 | A | 1/1976 | Gerns |
| 4,030,933 | A | 6/1977 | Conciatori et al. |
| 5,674,969 | A | 10/1997 | Sikkema et al. |
| 5,703,264 | A | 12/1997 | Yoshida et al. |
| 5,703,274 | A | 12/1997 | Gelmont et al. |
| 6,245,929 | B1 | 6/2001 | Soloveichik et al. |

FOREIGN PATENT DOCUMENTS

| | | |
|---|---|---|
| AT | 265 244 | 10/1968 |
| DE | 1812703 | 8/1969 |
| GB | 1 238 244 | 7/1971 |
| IL | 112 706 A1 | 4/1998 |
| IL | 112706 | 4/1998 |
| WO | 2006104974 A1 | 10/2006 |

OTHER PUBLICATIONS

T.Singh, S.N.Bedi, Di-xanthones. Part I. Chromono-2':3'-2:3-xanthone, Jour.Indian Chem.Soc., 1957, vol. 34, No. 4, pp. 321-323.*
I. Rusonik, H.Cohen, D.Meyerstein, Cu(I)(2,5,8,11-tetramethyl-2,5,8,11-tetraazadodecane) as a catalyst for Ullman's reaction, Dalton Transactions, 2003, 10, pp. 2024-2028.*
Adolf Marzin, 2,5-Dibromotoluic Acid, Journal Fuer Praktische Chemie, 1933, pp. 103-106.
Tara Singh et al., DI-Xanthones. Part 1. Chromono-2'.3'-2:3-Xanthone, Jour. Indian Chem. Soc., 1957, vol. 34:321-323.

Irena Rusonik et al., CU(I)(2,5,8,11-Tetramethyl-2,5,8,11-Tetraazadodecane) + as a Catalyst for Ullmann's Reaction, Dalton Transactions, 2003, pp. 2024-2028.
Rolando F. Pellon Comdom et al., Synthesis of Salicyclic Acid Derivatives From the Corresponding 2-Chlorbenzoic Acid Using Water as Solvent, Synthetic Communications, 2002, vol. 32:2055-2059.
J. E. Mcintyre et al., The Oxidation of Alkylaromatic Compounds in Aqueous Hydrogen Bromide, Journal of the Chemical Society, Abstracts, 1961, pp. 4082-4085.
F. F. Shcherbina et al., Liquid-Phase Oxidation of 2,5-Dichloro-P-Xylene, Zhurnal Prikladnoi Khimii, Sankt-Peterburg, Russian Federation, 1990, vol. 63:467-470.
Robert J. Perry et al., Synthesis of Polyimides Via the Palladium-Catalyzed Carbonylation of BIS(O-IODO Esters) and Diamines, Macromolecules, 1995, vol. 28:3509-3515.
Magal Saphier et al., Copper(I) as a Homogeneous Catalyst for the Ullmann Reaction in Aqueous Solutions—the Transformation of 2-Bromobenzoate Into Salicylate.
Mark Gelmont et al., A New Route for the Preparation of 5-Hydroxyisophthalic Acid, Organic Process Research & Development, 2002, vol. 6:591-596.
Yoel Sasson et al., Liquid-Phase Oxidation of Deactivated Methylbenzenes by Aqueous Sodium Hypochlorite Catalyzed by Ruthenium Salts Under Phase-Transfer, Journal of Organic Chemistry, 1986, vol. 51:2880-2883.
Ruggli et al., A New Linear Benzodipicoline, 2,6-Dimethyl-1,5-Anthrazoline, 51ST Communication Concerning Nitrogen Heterocycles, Basel University Institute for Organic Chemistry, Basel Switzerland, Jan. 6, 1944.
Keith W. Anderson et al., The Selection Reaction of Aryl Halides With KOH: Synthesis of Phenols, Aromatic Ethers, and Benzofurans; J. Am. Chem. Soc., 2003, vol. 128:10694-10695.
M. Lammers et al., Mechanical Properties and Structural Transitions in the New Rigid-Rod Polymer Fibre PIPD ("M5") During the Manufacturing Process, Polymer, 1998, vol. 39:5999-6005.
Doetze J. Sikkema, Design, Synthesis and Properties of a Novel Rigid Rod Polymer, PIPD or "5": High Modulus and Tenacity Fibres With Substantial Compressive Strength, Polymer, 1998, vol. 39:5981-5986.
Doetze J. Sikkema, Manmade Fibers One Hundred Years: Polymers and Polymer Design, Journal of Applied Polymer Science, 2002, vol. 83:484-488.
International Search Report, Dated Mar. 28, 2008, International Application No. PCT/US2007/024467, International Filing Date: Nov. 28, 2007.
Marzin A: "Zur Kenntnis Der 2,5-Dibromtoluyls Ure" Chemiker Zeitug, Huethig Verlag, Heidelberg, DE, vol. 138 No. 4-5 (Aug. 19, 1993) pp. 103-103, XP008089408.
Singh, Tara and Bedi, S.N.: "Di-Xanthones; Part I. Chromono-2' :3' -2:3-Xanthone" J. of the Indian Chemical Society, vol. 34, No. 4, 1957, pp. 321-323, XP008089434.
Rusonik, Irena et al., "CU(I)(2,5,8,11-Tetramethyl -2,5,8, 11-Tetra Azadodecane)+ as a Catalyst for Ullmann's Reaction" Dalton Transactions, (10), 2024, 2028, Coden: DTARAF; ISSN: 1477-9226, 2003, XP002472757.

(Continued)

*Primary Examiner*—Daniel M Sullivan
*Assistant Examiner*—Sudhakar Katakam

(57) ABSTRACT

2,5-dihydroxyterephthalic acid is produced in high yields and high purity from 2,5-dihaloterephthalic acid by contact with a copper source and a ligand that coordinates to copper under basic conditions.

20 Claims, No Drawings

OTHER PUBLICATIONS

Comdom, Rolando F. Pellon et al., "Synthesis of Salicylic Acid Derivatives From the Corresponding 2- Chlorobenzoic Acid Using Water as Solvent" Synthetic Communications, 32 (13), 2055-2059 Coden: SYNCAV; ISSN: 0039-7911, 2002, XP002472756.

Zhang, Hui et al., "Amino Acid Promoted Cui-Catalyzed C-N Bond Formation Between Aryl Halides and Amines or N-Containing Heterocycles" Journal of Organic Chemistry, 70(13), 5164-5173 Coden: JOCEAH; ISSN: 0022-3263, 2005, XP002472753.

Csuk Rene et al., "Convenient Access to Substitued Acridines by a Buchwald-Hartwig Amination" Tetrahedron, 60(27), 5737-5750 Coden: TATRAB; ISSN: 0040-4020, 2004, XP002472754.

Ma, Daweit et al., "Mild Method for Ullmann Coupling Reaction of Amines and Aryl Halides" Organic Letters, 5(14), 2453-2455 Coden: ORLEF7; ISSN: 1523-7060, 2003, XP002472755.

U.S. Appl. No. 11/604,942, filed Nov. 28, 2006, Joachim C. Ritter.
U.S. Appl. No. 11/604,936, filed Nov. 28, 2006, Joachim C. Ritter.
U.S. Appl. No. 11/604,937, filed Nov. 28, 2006, Joachim C. Ritter.
U.S. Appl. No. 11/604,938, filed Nov. 28, 2006, Joachim C. Ritter.
U.S. Appl. No. 11/604,939, filed Nov. 28, 2006, Joachim C. Ritter.
U.S. Appl. No. 11/604,940, filed Nov. 28, 2006, Joachim C. Ritter.
U.S. Appl. No. 11/604,941, filed Nov. 28, 2006, Joachim C. Ritter.
U.S. Appl. No. 60/665,737, filed Mar. 28, 2005, Steven R. Allen et al.

* cited by examiner

PROCESS FOR THE SYNTHESIS OF 2,5-DIHYDROXYTEREPHTHALIC ACID

This application is a division of and claims the benefit of U.S. application Ser. No. 11/604,935, filed Nov. 28, 2006, which by this reference is incorporated in its entirety as a part hereof for all purposes.

TECHNICAL FIELD

This invention relates to the manufacture of hydroxybenzoic acids, which are valuable for a variety of purposes such as use as intermediates or as monomers to make polymers.

BACKGROUND

Hydroxybenzoic acids are useful as intermediates in the manufacture of many valuable materials including pharmaceuticals and compounds active in crop protection, and are also useful as monomers in the production of polymers. In particular, 2,5-dihydroxyterephthalic acid (Formula I, "DHTA") is a useful monomer for the synthesis of high strength fibers such as those made from poly[(1,4-dihydrodiimidazo[4,5-b:4',5'-e]pyridine-2,6-diyl) (2,5-dihydroxy-1,4-phenylene)].

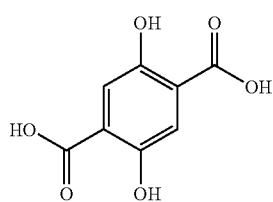

I

Various preparations of 2,5-dihydroxyterephthalic acid and other hydroxybenzoic acids are known. Marzin, in *Journal fuer Praktische Chemie*, 1933, 138, 103-106, teaches the synthesis of 2,5-dihydroxyterephthalic acid from 2,5-dibromoterephthalic acid (Formula II, "DBTA") in the presence of copper powder.

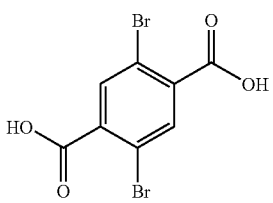

II

Singh et al, in *Jour. Indian Chem. Soc.*, Vol. 34, No. 4, pages 321-323 (1957), report the preparation of a product that includes DHTA by the condensation of DBTA with phenol in the presence of KOH and copper powder.

Rusonik et al, *Dalton Transactions*, 2003, 2024-2028, describe the transformation of 2-bromobenzoic acid into salicylic acid, benzoic acid, and diphenoic acid in a reaction catalyzed by Cu(I) in the presence of various ligands. A tertiary tetraamine minimizes the formation of diphenoic acid in use with Cu(I).

Comdom et al, *Synthetic Communications*, 32(13), 2055-59 (2002), describe a process for the synthesis of salicylic acids from 2-chlorobenzoic acids. Stoichiometric amounts of pyridine (0.5 to 2.0 moles per mole of 2-chlorobenzoic acid) are used such as at least 1.0 mole pyridine per mole 2-chlorobenzoic acid.

Cu powder is used as a catalyst along with the pyridine.

The various prior art processes for making hydroxybenzoic acids are characterized by long reaction times, limited conversion resulting in significant productivity loss, or the need to run under pressure and/or at higher temperatures (typically 140 to 250° C.) to get reasonable rates and productivity. A need therefore remains for a process by which 2,5-dihydroxy terephthalic acid can be produced economically; with low inherent operational difficulty; and with high yields and high productivity in both small- and large-scale operation, and in batch and continuous operation.

SUMMARY

One embodiment of this invention provides a process for preparing 2,5-dihydroxyterephthalic acid by (a) contacting a 2,5-dihaloterephthalic acid (III)

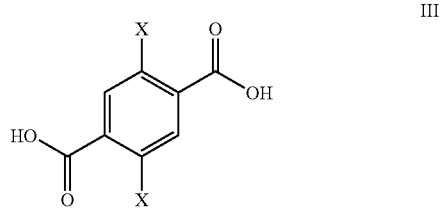

III where X=Cl, Br, or I with base in water to form therefrom the corresponding dibasic salt of 2,5-dihaloterephthalic acid; (b) contacting the dibasic salt of 2,5-dihaloterephthalic acid with base in water, and with a copper source in the presence of a ligand that coordinates to copper, to form the dibasic salt of 2,5-dihydroxyterephthalic acid from the dibasic salt of 2,5-dihaloterephthalic acid at a solution pH of at least about 8; (c) optionally, separating the dibasic salt of 2,5-dihydroxyterephthalic acid from the reaction mixture in which it is formed; and (d) contacting the dibasic salt of 2,5-dihydroxyterephthalic acid with acid to form therefrom 2,5-dihydroxyterephthalic acid.

In another embodiment, the ligand may be an amine ligand, and in a further embodiment the ligand includes, when it is a tetraamine ligand, at least one primary or secondary amino group.

Yet another embodiment of this invention provides a process for preparing a 2,5-dialkoxyterephthalic acid by preparing a 2,5-dihydroxyterephthalic acid in the manner described above and then converting the 2,5-dihydroxyterephthalic acid to a 2,5-dialkoxyterephthalic acid.

Yet another embodiment of this invention consequently provides a process for preparing 2,5-dialkoxyterephthalic acid by (a) contacting a 2,5-dihaloterephthalic acid (III)

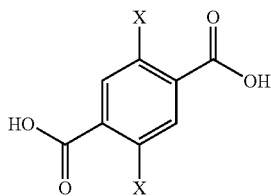

where X=Cl, Br, or I with base in water to form therefrom the corresponding dibasic salt of 2,5-dihaloterephthalic acid; (b) contacting the dibasic salt of 2,5-dihaloterephthalic acid with base in water, and with a copper source in the presence of a ligand that coordinates to copper, to form the dibasic salt of 2,5-dihydroxyterephthalic acid from the dibasic salt of 2,5-dihaloterephthalic acid at a solution pH of at least about 8; (c) optionally, separating the dibasic salt of 2,5-dihydroxyterephthalic acid from the reaction mixture in which it is formed; (d) contacting the dibasic salt of 2,5-dihydroxyterephthalic acid with acid to form therefrom a 2,5-dihydroxyterephthalic acid; and (e) converting the 2,5-dihydroxyterephthalic acid to a 2,5-dialkoxyterephthalic acid.

Yet another embodiment of this invention provides a process for preparing a 2,5-dihydroxyterephthalic acid or a 2,5-dialkoxyterephthalic acid as described above that further includes a step of subjecting the 2,5-dihydroxyterephthalic acid or the 2,5-dialkoxyterephthalic acid to a reaction to prepare therefrom a compound, monomer, oligomer or polymer.

Yet another embodiment of this invention consequently provides a process for preparing a compound, monomer, oligomer or polymer by (a) contacting a 2,5-dihaloterephthalic acid (III)

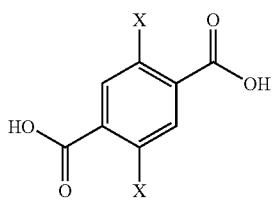

where X =Cl, Br, or I with base in water to form therefrom the corresponding dibasic salt of 2,5-dihaloterephthalic acid; (b) contacting the dibasic salt of 2,5-dihaloterephthalic acid with base in water, and with a copper source in the presence of a ligand that coordinates to copper, to form the dibasic salt of 2,5-dihydroxyterephthalic acid from the dibasic salt of 2,5-dihaloterephthalic acid at a solution pH of at least about 8; (c) optionally, separating the dibasic salt of 2,5-dihydroxyterephthalic acid from the reaction mixture in which it is formed; (d) contacting the dibasic salt of 2,5-dihydroxyterephthalic acid with acid to form therefrom 2,5-dihydroxyterephthalic acid; (e) optionally, converting the 2,5-dihydroxyterephthalic acid to a 2,5-dialkoxyterephthalic acid; and (f) subjecting the 2,5-dihydroxyterephthalic acid and/or the 2,5-dialkoxyterephthalic acid to a reaction to prepare therefrom a compound, monomer, oligomer or polymer.

DETAILED DESCRIPTION

This invention provides a high yield and high productivity process for preparing a 2,5-dihydroxyterephthalic acid by contacting a 2,5-dihaloterephthalic acid with base to form the dibasic salt of 2,5-dihaloterephthalic acid; contacting the dibasic salt of 2,5-dihaloterephthalic acid with base, and with a copper source in the presence of an amine ligand that coordinates to copper, to form the dibasic salt of 2,5-dihydroxyterephthalic acid; and then contacting the dibasic salt of 2,5-dihydroxyterephthalic acid with acid to form the 2,5-dihydroxyterephthalic acid product. The term "dibasic salt" as used herein denotes the salt of a dibasic acid, which is an acid that contains two replaceable hydrogen atoms per molecule.

Suitable dihaloterephthalic acids with which the process of this invention is started include 2,5-dibromoterephthalic acid, 2,5-dichloroterephthalic acid, and 2,5-diiodoterephthalic acid, or mixtures thereof. 2,5-dibromoterephthalic acid ("DBTA")is commercially available. It can, however, be synthesized, for example, by oxidation of p-xylene in aqueous hydrogen bromide (McIntyre et al, *Journal of the Chemical Society*, Abstracts, 1961, 4082-5), by bromination of terephthalic acid or terephthaloyl chloride (U.S. Pat. No. 3,894,079), or by oxidation of 2,5-dibromo-1,4-dimethylbenzene (DE 1,812,703). 2,5-dichloroterephthalic acid is also commercially available. It can, however, be synthesized, for example, by oxidation of 2,5-dichloro-1,4-dimethylbenzene [Shcherbina et al, *Zhurnal Prikladnoi Khimii* (Sankt-Peterburg, Russian Federation, 1990)], 63(2), 467-70. 2,5-diiodoterephthalic acid can be synthesized, for example, by oxidation of 2,5-diiodo-1,4-dimethylbenzene [Perry et al, *Macromolecules* (1995), 28(10), 3509-15].

In step (a), 2,5-dihaloterephthalic acid is contacted with base in water to form therefrom the corresponding dibasic salt of 2,5-dihaloterephthalic acid. In step (b), the dibasic salt of 2,5-dihaloterephthalic acid is contacted with base in water, and with a copper source in the presence of a ligand that coordinates to copper, to form the dibasic salt of 2,5-dihydroxyterephthalic acid from the dibasic salt of 2,5-dihaloterephthalic acid.

The base used in step (a) and/or step (b) may be an ionic base, and may in particular be one or more of a hydroxide, carbonate, bicarbonate, phosphate or hydrogen phosphate of one or more of Li, Na, K, Mg or Ca. The base used may be water-soluble, partially water-soluble, or the solubility of the base may increase as the reaction progresses and/or as the base is consumed. NaOH and $Na_2CO_3$ are preferred, but other suitable organic bases may be selected, for example, from the group consisting of trialkylamines (such as tributylamine); N,N,N',N'-tetramethylethylenediamine; and N-alkyl imidazoles (for example, N-methylimidazole). In principle any base capable of maintaining a pH above 8 and/or binding the acid produced during the reaction of the 2,5-dihaloterephthalic acid is suitable.

The specific amounts of base to be used in steps (a) and/or (b) depend on the strength of the base. In step (a), 2,5-dihaloterephthalic acid is preferably contacted with at least about two equivalents of base, preferably a water-soluble base, per equivalent of 2,5-dihaloterephthalic acid. One "equivalent" as used for a base in this context is the number of moles of base that will react with one mole of hydrogen ions; for an acid, one equivalent is the number of moles of acid that will supply one mole of hydrogen ions.

In step (b), enough base should be used to maintain a solution pH of at least about 8, or at least about 9, or at least about 10, and preferably between about 9 and about 11. Thus, typically in step (b), the dibasic salt of 2,5-dihaloterephthalic acid is contacted with at least about two equivalents of base, such as a water-soluble base, per equivalent of the dibasic salt of 2,5-dihaloterephthalic acid.

In alternative embodiments, however, it may be desirable in steps (a) and (b) to use a total of at least about 4 to about 5 equivalents of base, such as a water-soluble base, in the reaction mixture per equivalent of 2,5-dihaloterephthalic acid originally used at the start of the reaction. A base used in an amount as described above is typically a strong base, and is typically added at ambient temperature. The base used in step (b) may be the same as, or different than, the base used in step (a).

As mentioned above, in step (b), the dibasic salt of 2,5-dihaloterephthalic acid is also contacted with a copper source in the presence of a ligand that coordinates to copper. The copper source and the ligand may be added sequentially to the reaction mixture, or may be combined separately (for example, in a solution of water or acetonitrile) and added together. The copper source may be combined with the ligand in the presence of oxygen in water, or be combined with a solvent mixture containing water.

From the presence together in the reaction mixture of the copper source and the ligand, in a basic solution of the dibasic salt of the 2,5-dihaloterephthalic acid, there is obtained an aqueous mixture containing the dibasic salt of 2,5-dihydroxyterephthalic acid, copper specie(s), the ligand, and a halide salt. If desired, the dibasic salt of 2,5-dihydroxyterephthalic acid may, at this stage and before the acidification in step (d), be separated from the mixture [as optional step (c)], and may be used as a dibasic salt in another reaction or for other purposes.

The dibasic salt of 2,5-dihydroxyterephthalic acid is then contacted in step (d) with acid to convert it to the 2,5-dihydroxyterephthalic acid product. Any acid of sufficient strength to protonate the dibasic salt is suitable. Examples include without limitation hydrochloric acid, sulfuric acid and phosphoric acid.

The reaction temperature for steps (a) and (b) is preferably between about 40 and about 120° C., more preferably between about 75 and about 95° C.; and the process thus in various embodiments involves a step of heating the reaction mixture. The solution is typically allowed to cool before the acidification in step (d) is carried out. In various embodiments, oxygen may be excluded during the reaction.

The copper source is copper metal ["Cu(0)"], one or more copper compounds, or a mixture of copper metal and one or more copper compounds. The copper compound may be a Cu(I) salt, a Cu(II) salt, or mixtures thereof. Examples include without limitation CuCl, CuBr, CuI, $Cu_2SO_4$, $CuNO_3$, $CuCl_2$, $CuBr_2$, $CuI_2$, $CuSO_4$, and $Cu(NO_3)_2$. CuBr is preferred. The amount of copper provided is typically about 0.1 to about 5 mol % based on moles of 2,5-dihaloterephthalic acid.

When the copper source is Cu(0), Cu(0), copper bromide and a ligand may be combined in the presence of air. In the case of Cu(0) or Cu(I), a predetermined amount of metal and ligand may be combined in water, and the resulting mixture may be reacted with air or dilute oxygen until a colored solution is formed. The resulting metal/ligand solution is added to the reaction mixture containing the dibasic salt of 2,5-dihaloterephthalic acid and base in water.

The ligand may be a straight- or branched-chain or cyclic, aliphatic or aromatic, substituted or unsubstituted, amine, or a mixture of two of more such ligands. Whether formed as a compound, an oligomer or polymer, conventional nomenclature may be used to describe the number of amine groups present in the ligand, such as a mono-, di-, tri-, tetra-, penta-, hexa-, hepta- or octaamine, and so on. In its unsubstituted form, the ligand may be an organoamine that contains carbon, nitrogen and hydrogen atoms only. In it substituted form, the amine ligand may contain hetero atoms such as oxygen or sulfur. In various embodiments, particularly but not exclusively as relates to the tetraamines, the amine may contain at least one primary or secondary amino group.

Primary or secondary monoamines suitable for use herein as the ligand include those described generally by the following Formula 11

11 wherein $R^1$ and $R^2$ are each independently selected from H;

a $C_1$–$C_{10}$ straight-chain or branched, saturated or unsaturated, substituted or unsubstituted, hydrocarbyl radical;

a $C_3$–$C_{12}$ cyclic aliphatic, saturated or unsaturated, substituted or unsubstituted, hydrocarbyl radical; or a $C_6$–$C_{12}$ aromatic substituted or unsubstituted hydrocarbyl radical.

In certain embodiments, $R^1$ and/or $R^2$ may for example be a methyl, ethyl, propyl, butyl, pentyl, hexyl or phenyl radical. In other embodiments, at least one of $R^1$ and $R^2$ is not H. Particular monoamines suitable for use herein as the ligand include ethyl amine, isopropylamine, sec-butyl amine, dimethyl amine, methyl ethyl amine, ethyl-n-butyl amine, allylamine, cyclohexyl amine, N-ethylcyclohexyl amine, aniline, N-ethyl aniline, toluidine and xylidine.

Primary or secondary diamines suitable for use herein as the ligand include those described generally by the following Formula 12

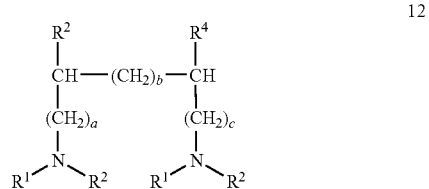

12 wherein each $R^1$ and each $R^2$ is independently H;

a $C_1$–$C_{10}$ straight-chain or branched, saturated or unsaturated, substituted or unsubstituted, hydrocarbyl radical;

a $C_3$–$C_{12}$ cyclic aliphatic, saturated or unsaturated, substituted or unsubstituted, hydrocarbyl radical; or a $C_6$–$C_{12}$ aromatic substituted or unsubstituted hydrocarbyl radical; or wherein $R^3$ and $R^4$ are each independently H;

a $C_1$–$C_{10}$ straight-chain or branched, saturated or unsaturated, substituted or unsubstituted, hydrocarbyl radical;

a $C_3$–$C_{12}$ cyclic aliphatic, saturated or unsaturated, substituted or unsubstituted, hydrocarbyl radical; or a $C_6$~$C_{12}$ aromatic substituted or unsubstituted hydrocarbyl radical; or $R^3$ and $R^4$ are joined to form a ring structure that is a $C_4$~$C_{12}$ aliphatic, saturated or unsaturated, substituted or unsubstituted, hydrocarbyl ring structure; or a $C_6$~$C_{12}$ aromatic substituted or unsubstituted hydrocarbyl ring structure; and wherein a, b, and c are each independently 0~4.

In certain embodiments, one or both of the $R^1$s is H. In other embodiments, one or both of the $R^2$s is also H. In other embodiments, any one or more of $R^1$ to $R^4$ may be a methyl, ethyl, propyl, butyl, pentyl, hexyl or phenyl radical.

In various particular embodiments, a, b and c may all equal 0, and either $R^3=R^4=H$, or $R^3$ and $R^4$ are joined to form an aliphatic ring structure. Particularly when b=0, the aliphatic ring structure may be a cyclohexylene group, which is the divalent radical, —$C_6H_{10}$—, as shown below, thus providing a cyclohexyl diamine:

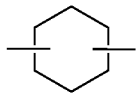

The formation of a cyclohexylene group from $R^3$ and $R^4$ may be illustrated generally by the following structure:

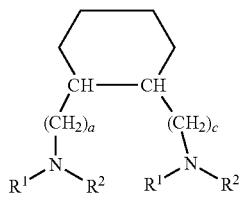

where $R^1$, $R^2$, a and c are as set forth above. In alternative embodiments, however, one amino group, or the alkyl radical on which it is located, may be in the meta or para position on the cycloalkyl or aromatic ring to the other amino group.

Suitable aliphatic diamines may include N,N'-di-n-alkylethylene diamines and N,N'-di-n-alkylcyclohexane-1,2-diamines. Specific examples include without limitation N,N'-dimethylethylene diamine, N,N'-diethylethylene diamine, N,N'-di-n-propylethylene diamine, N,N'-dibutylethylene diamine, N,N'-dimethylcyclohexane-1,2-diamine, N,N'-diethylcyclohexane-1,2-diamine, N,N'-di-n-propylcyclohexane-1,2-diamine, and N,N'-dibutylcyclohexane-1,2-diamine. Examples of suitable aromatic diamines include without limitation 1,2-phenylenediamine and N,N'-dialkylphenylene diamines such as N,N'-dimethyl-1,2-phenylenediamine and N,N'-diethyl-1,2-phenylenediamine; and benzidine.

Primary or secondary tri- and higher amines suitable for use herein as the ligand may be described generally by the following Formula 13:

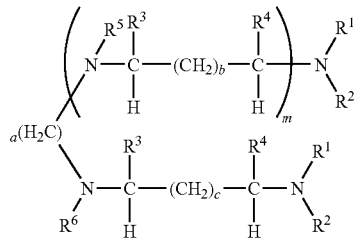

wherein each $R^1$, $R^2$, $R^3$, $R^4$, $R^5$ and $R^6$ is independently selected from;

H;

a $C_1$~$C_{10}$ straight-chain or branched, saturated or unsaturated, substituted or unsubstituted, hydrocarbyl radical;

a $C_3$~$C_{12}$ cyclic aliphatic, saturated or unsaturated, substituted or unsubstituted, hydrocarbyl radical; or a $C_6$~$C_{12}$ aromatic substituted or unsubstituted hydrocarbyl radical; and wherein a is 2~4, b and c is each independently 0~4; and $m \geq 0$.

In certain embodiments, one or both of the $R^1$s, or at least one $R^3$, or at least one $R^4$, or $R^5$, and/or $R^6$ is H. In other particular embodiments, m=0, 1, 2, 3, 4 or 5. In yet other embodiments, $R^3=R^4=R^6=H$; and/or one or both of $R^1$ and $R^2=H$. In further embodiments, any one or more of $R^1$ through $R^5$ may be a methyl, ethyl, propyl, butyl, pentyl, hexyl or phenyl radical.

Amines according to Formula 13 suitable for use herein as the ligand include, for example, those described generally by the following Formula 14:

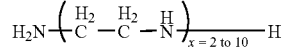

wherein x is 2~10. Formula 14 describes various polyethyleneamines where, in Formula 13, each R group is H, a=2, b=c=0, and m=0 to 8.

Other amines according to Formula 13, or other higher amines, suitable for use herein as the ligand include diethylenetriamine and triethylenetetramine, as well as those described generally by the following structures:

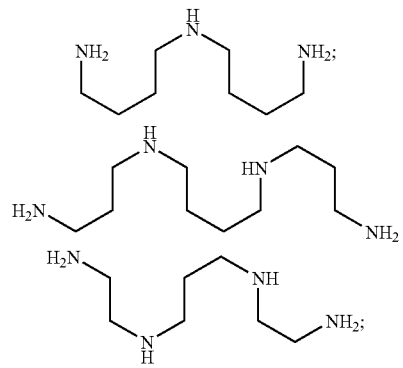

-continued

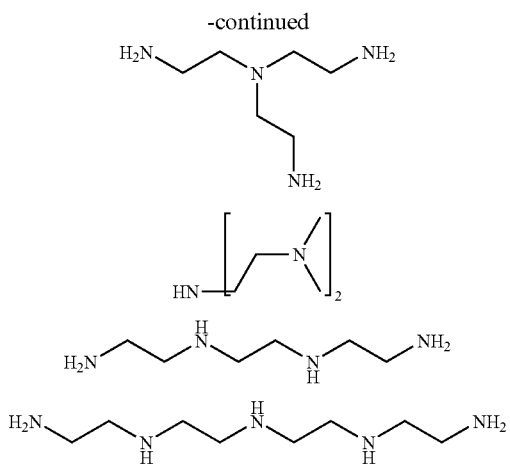

The ligand may also be a cyclic amine compound that is a molecule having at least one closed ring structure in which at least one ring atom is nitrogen. This form of ligand is then heterocyclic in the sense that the ring structure will contain, in addition to nitrogen atoms, other atoms that are primarily carbon and hydrogen, but may also be oxygen and/or sulfur, as described below. The nitrogen atom may for example be a member of a $C_4$~$C_{12}$ aliphatic, saturated or unsaturated, substituted or unsubstituted hydrocarbyl ring structure; or a $C_5$~$C_{12}$ aromatic, substituted or unsubstituted hydrocarbyl ring structure.

Examples of various nitrogen-containing, cyclic compounds suitable for use herein as the ligand include without limitation quinolione, indole, imidazole, ethylenimine, as well as those described by the following structures:

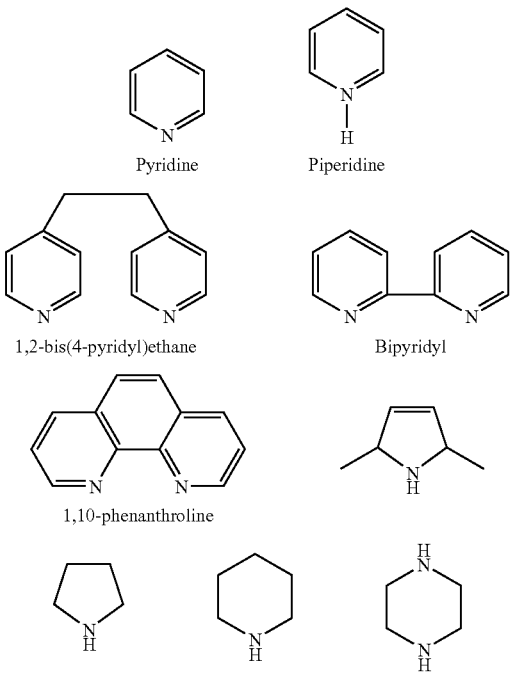

-continued

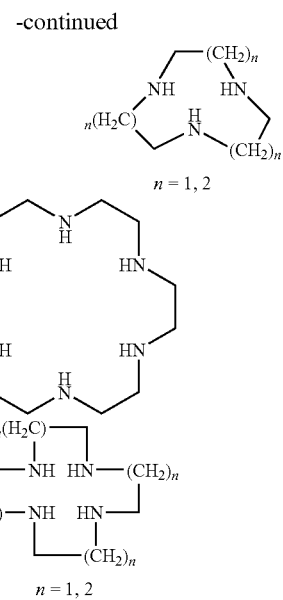

The "hydrocarbyl" groups referred to above in the descriptions of ligands suitable for use herein are, when unsubstituted, univalent groups containing only carbon and hydrogen. Similarly, an unsubstituted amine is a compound that contains in its structure nitrogen, carbon and hydrogen atoms only. In any of the hydrocarbyl radicals or ring structures described above, however, one or more O or S atoms may optionally be substituted for any one or more of the in-chain or in-ring carbon atoms, provided that the resulting structure contains no —O—O— or —S—S— moieties, and provided that no carbon atom is bonded to more than one heteroatom. An example of a suitable ligand in which an oxygen atom has been substituted for a carbon atom is shown in Formula 15:

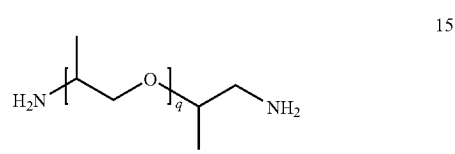

wherein q may have, for example, an average value of about 3 in a mixture of molecules with different molecular weights.

Other examples of ligands suitable for use herein and having oxygen substitution include anisidine, phenetidine, as well as those described generally by the following structures:

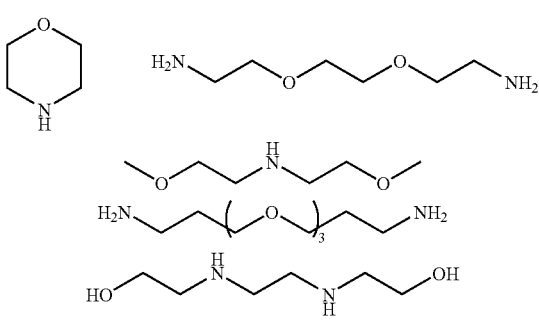

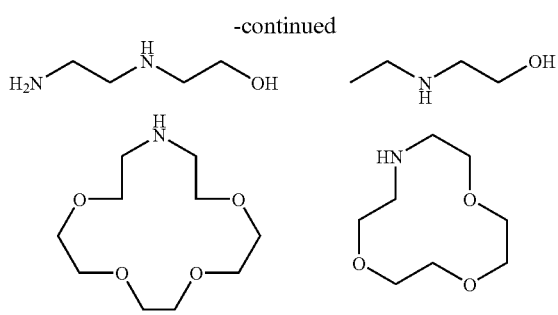

Ligands of particular versatility include secondary amines, particularly N,N'-substituted 1,2-diamines, including those that that may be described as $R^7NH-(CHR^8CHR^9)-NHR^{10}$ wherein $R^7$ and $R^{10}$ are each independently chosen from the group of $C_1$-$C_4$ primary alkyl radicals, and $R^8$ and $R^9$ are each independently chosen from the group of H and $C_1$-$C_4$ alkyl radicals, and/or where $R^8$ and $R^9$ may be joined to form a ring structure.

When, in Formula 12, $R^3$ and $R^4$ are joined to form an aromatic ring structure, and/or when a cyclic amine ligand contains one or more aromatic ring structures, more severe reaction conditions (e.g. higher temperature, or larger amounts of copper and/or ligand) may be needed to achieve high conversion, selectivity, yield and/or purity in the reaction.

A ligand suitable for use herein may be selected as any one or more or all of the members of the whole population of ligands described by name or structure above. A suitable ligand may, however, also be selected as any one or more or all of the members of a subgroup of the whole population, where the subgroup may be any size (1, 2, 6, 10 or 20, for example), and where the subgroup is formed by omitting any one or more of the members of the whole population as described above. As a result, the ligand may in such instance not only be selected as one or more or all of the members of any subgroup of any size that may be formed from the whole population of ligands as described above, but the ligand may also be selected in the absence of the members that have been omitted from the whole population to form the subgroup. For example, in certain embodiments, the ligand useful herein may be selected as one or more or all of the members of a subgroup of ligands that excludes from the whole population pyridine, 2,5,8,11-tetramethyl-2,5,8,11-tetraazadodecane, and/or 1,1,4,7,10,10-hexamethyltriethylenetetraamine, with or without the exclusion from the whole population of other ligands too.

In various embodiments, the ligand may be provided in an amount of about 1 to about 8, preferably about 1 to about 2, molar equivalents of ligand per mole of copper. In those and other embodiments, the ratio of molar equivalents of ligand to molar equivalents of dihaloterephthalic acid may be less than or equal to about 0.1. As used herein, the term "molar equivalent" indicates the number of moles of ligand that will interact with one mole of copper.

In one embodiment, a Cu(I) salt may be selected as CuBr; the ligand is selected from the group consisting of N,N'-dimethylethylene diamine, N,N'-diethylethylene diamine, N,N'-di-n-propylethylene diamine, N,N'-dibutylethylene diamine, N,N'-dimethylcyclohexane-1,2-diamine, N,N'-diethylcyclohexane-1,2-diamine, N,N'-di-n-propylcyclohexane-1,2-diamine, N,N'-dibutylcyclohexane-1,2-diamine; and CuBr is combined with two molar equivalents of the ligand in the presence of water and air.

The ligand is believed to facilitate the action of the copper source as a catalyst, and/or the copper source and the ligand are believed to function together to act as a catalyst, to improve one or more attributes of the reaction.

The process described above also allows for effective and efficient synthesis of related compounds, such as a 2,5-dialkoxy terephthalic acid, which may be described generally by the structure of Formula VI:

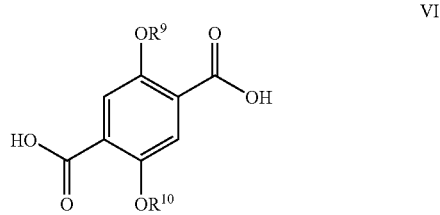

wherein $R^9$ and $R^{10}$ are each independently a substituted or unsubstituted $C_{1-10}$ alkyl group. $R^9$ and $R^{10}$ are, when unsubstituted, univalent groups containing only carbon and hydrogen. In any of those alkyl groups, however, one or more O or S atoms may optionally be substituted for any one or more of the in-chain carbon atoms, provided that the resulting structure contains no —O—O— or —S—S— moieties, and provided that no carbon atom is bonded to more than one heteroatom.

A 2,5-dihydroxy terephthalic acid, as prepared by the process of this invention, may be converted to a 2,5-dialkoxy terephthalic acid, and such conversion may be accomplished, for example, by contacting a 2,5-dihydroxy terephthalic acid under basic conditions with a dialkyl sulfate of the formula $R^9R^{10}SO_4$. One suitable method of running such a conversion reaction is as described in Austrian Patent No. 265,244. Suitable basic conditions for such conversion are a solution pH of at least about 8, or at least about 9, or at least about 10, and preferably about 9 to about 11, using one or more bases such as described above.

In certain embodiments, it may be desired to separate the 2,5-dihydroxyterephthalic acid from the reaction mixture in which it was formed before converting it to a 2,5-dialkoxyterephthalic acid.

The process described above also allows for effective and efficient synthesis of products made from the resulting 2,5-dihydroxyterephthalic acid or 2,5-dialkoxyterephthalic acid such as a compound, a monomer, or an oligomer or polymer thereof. These produced materials may have one or more of ester functionality, ether functionality, amide functionality, imide functionality, imidazole functionality, carbonate functionality, acrylate functionality, epoxide functionality, urethane functionality, acetal functionality, and anhydride functionality.

Representative reactions involving a material made by the process of this invention, or a derivative of such material, include, for example, making a polyester from a 2,5-dihydroxyterephthalic acid and either diethylene glycol or triethylene glycol in the presence of 0.1% of $ZN_3(BO_3)_2$ in 1-methylnaphthalene under nitrogen, as disclosed in U.S. Pat. No. 3,047,536 (which is incorporated in its entirety as a part hereof for all purposes). Similarly, a 2,5-dihydroxyterephthalic acid is disclosed as suitable for copolymeriztion with a dibasic acid and a glycol to prepare a heat-stabilized polyester in U.S. Pat. No. 3,227,680 (which is incorporated in its entirety as a part hereof for all purposes), wherein representative conditions involve forming a prepolymer in the presence of titanium tetraisopropoxide in butanol at 200–250° C., followed by solid-phase polymerization at 280° C. at a pressure of 0.08 mm Hg.

A 2,5-dihydroxyterephthalic acid has also been polymerized with the trihydrochloride-monohydrate of tetraaminopyridine in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Provisional Application Ser. No. 60/665,737, filed Mar. 28, 2005 (which is incorporated in its entirety as a part hereof for all purposes), published as WO 2006/104974. The polymer that may be so produced may be a pyridobisimidazole-2,6-diyl(2,5-dihydroxy-p-phenylene) polymer such as a poly(1,4-(2,5-dihydroxy) phenylene-2,6-pyrido[2,3-d: 5,6-d']bisimidazole) polymer. The pyridobisimidazole portion thereof may, however, be replaced by any or more of a benzobisimidazole, benzobisthiazole, benzobisoxazole, pyridobisthiazole and a pyridobisoxazole; and the 2,5-dihydroxy-p-phenylene portion thereof may be replace the derivative of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole.

EXAMPLES

This invention is further defined in the following examples. These examples, while indicating preferred embodiments of the invention, are given by way of illustration only, and do not limit the scope of the appended claims. From the above discussion and these examples, the essential characteristics of this invention may be ascertained, and, without departing from the spirit and scope thereof, modifications of the invention may be made to adapt it to various uses and conditions.

The following materials were used in the examples. All reagents were used as received. Product purity was determined by $^1$H NMR.

The ligands listed in Table 1 (labeled A through O, Q and R) were obtained from Aldrich Chemical Company (Milwaukee, Wis.). Ligand P was obtained from TCI America (Portland, Oreg.).

TABLE 1

| Ligand Code | Ligand | Purity (%) |
|---|---|---|
| A | N,N-Dimethylethylenediamine | 95 |
| B | N,N'-Diethylethylenediamine | 95 |
| C | N,N'-Dimethyl-1,6-hexanediamine | 98 |
| D | N,N-Diethyl-N'-methyethylenediamine | 97 |
| E | 1,2-Phenylenediamine | 98 |
| F | rac-trans-N,N'-Dimethylcyclohexane-1,2-diamine | 97 |
| G | N-Methylethylenediamine | 95 |
| H | 1,2-Bis(4-pyridyl)ethane | 99 |
| I | N,N,N',N'-tetramethylethylenediamine | 99 |
| J | rac 1,2-Diaminocyclohexane | 99 |
| K | N,N'-Dimethylethylenediamine | 99 |
| L | 1,10-Phenanthroline | 99+ |
| M | Ethylenediamine diacetate | 98 |
| N | N,N'-Diisopropylethylene diamine | 99 |
| O | 1,1,4,7,10,10-Hexamethyltriethylenetetramine | 97 |

TABLE 1-continued

| Ligand Code | Ligand | Purity (%) |
|---|---|---|
| P | (1S,2S)-(+)-Dimethylcyclohexane-1,2-diamine | 95 |
| Q | Pyridine | >99 |
| R | Bipyridyl | >99 |

2,5-dibromoterephthalic acid (95+% purity), except that used in Example 1, was obtained from Maybridge Chemical Company Ltd.(Cornwall, United Kingdom ). The 2,5-dibromoterephthalic acid used in Example 1 was synthesized according to the method described in DE 1,812,703.

Copper(I) bromide ("CuBr") (98% purity) was obtained from Acros Organics (Geel, Belgium). Copper(II) bromide ("CuBr$_2$") (99% purity), copper(II) chloride ("CuCl$_2$") (97% purity), copper(I) triflate ("Cu(OTf)$_2$") (97% purity), and copper (II)triflate("Cu(OTf)")(98% purity) were obtained from Aldrich Chemical Company (Milwaukee, Wis., USA). Copper(II) sulfate ("CuSO$_4$") (98% purity) was obtained from Strem Chemicals, Inc. (Newburyport, Mass., USA). Copper powder (99.5% purity), spherical, approximately 100 mesh, was obtained from Alfa Aesar (Ward Hill, Mass.).

Acetonitrile (99.8% purity) and Na$_2$CO$_3$ (99.5% purity) were obtained from EM Science (Gibbstown, N.J.).

As used herein, the term "conversion" refers to how much reactant was used up as a fraction or percentage of the theoretical amount. The term "selectivity" for a product P refers to the molar fraction or molar percentage of P in the final product mix. The conversion multiplied by the selectivity thus equals the maximum "yield" of P; the actual or "net" yield will normally be somewhat less than this because of sample losses incurred in the course of activities such as isolating, handling, drying, and the like. The term "purity" denotes what percentage of the in-hand, isolated sample is actually the specified substance.

The terms "15% HCl" and "15% aqueous HCl" as used below denote aqueous hydrochloric acid whose concentration is 15 grams of HCl per 100 mL of solution. The terms "H$_2$O" and "water" refer to distilled water. The meaning of abbreviations is as follows: "g" means gram(s), "mg" means milligram(s), "h" means hour(s), "kPa" means kilopascal, "M" means molar, "min" means minute(s), "mL" means milliliter(s), "mmol" means millimole(s), "NMR" means nuclear magnetic resonance spectroscopy, and "psi" means pounds per square inch.

Example 1

Under nitrogen, 5.00 g (15.4 mmol) of 2,5-dibromoterephthalic acid was combined with 20 g of H$_2$O. 1.71 g (16.1 mmol) of Na$_2$CO$_3$ was then added. The mixture was heated to reflux with stirring for 30 min, remaining under a nitrogen atmosphere. Another 2.38 g (22.5 mmol) of Na$_2$CO$_3$ was added to the reaction mixture and reflux was continued for 30 min. Separately, 28 mg of CuBr and 50 mg of rac-trans-N,N'-dimethylcyclohexane-1,2-diamine (Ligand F) were combined with 2 mL H$_2$O under nitrogen. The resulting mixture was stirred under an air atmosphere until the CuBr was dissolved to give a blue-purple solution. This solution was added to the stirred reaction mixture at 90° C. under nitrogen and stirred for 2 h at 90° C. After cooling to 25° C., the reaction mixture was acidified with 15% HCl, producing a yellow precipitate. The yellow precipitate was filtered and washed with water. After drying, a total of 2.96 g (15 mmol, 97% yield) 2,5-dihydroxyterphtalic acid was collected. The purity was determined by $^1$H NMR to be >98%.

Example 2

In a round bottom flask with reflux condenser, 1.00 g (3.1 mmol) of 2,5-dibromoterephthalic acid was combined with 10 mL of $H_2O$. 0.85 g of $Na_2CO_3$ (7.8 mmol) was added to this mixture. Subsequently, 0.12 mL (0.031 mmol, 1 mol %) of 0.23 M copper(I) bromide in acetonitrile was added, followed by addition of 0.12 mL (0.062 mmol, 2 mol %) of 0.5 M rac-trans-N, N'-Dimethylcyclohexane-1,2-diamine (Ligand F). The reaction mixture was heated to 90° C. with stirring, then stirred for 18 h at 90° C. A sample was taken after 6 h and analyzed by $^1H$ NMR. No starting material was detected. After 18 h, the conversion of 2-bromo-5-hydroxyterephthalic acid was larger than 99%, and the product selectivity to 2,5-dihydroxyterephthalic acid was above 98%. After cooling to 25° C., the reaction mixture was acidified with 15% HCl, producing a light green precipitate. The precipitate was filtered and washed with water and dried. The water phase did not show any detectable organic products by $^1H$ NMR analysis. The purity of the solid product was determined to >98%.

Examples 3~19; Comparative Examples A and B

Under a nitrogen atmosphere, to a 2 mL vial with magnetic stir bar was added 25 mg (0.077 mmol) of 2,5-dibromoterephthalic acid ("DBTA"), followed by 0.308 mL (0.308 mmol) of 1.0 M aqueous sodium hydroxide and 0.169 mL (0.169 mmol) of 1.0 M aqueous sodium acetate. The mixture was then treated with 0.003 mL (0.00077 mol, 1 mol %) of 0.23 M copper(I) bromide in acetonitrile and 0.003 mL (0.00154 mmol, 2 mol %) of the diamine ligand as noted below in Table 2, or half the amount for tetraamine ligand (Comparative Example A) or twice the amount in the case of pyridine (Q). For Comparative Example B, no ligand was used.

The reactor vial was then sealed under nitrogen and placed in a sealed reactor block. After 3 hours at 90° C., the reaction mixture was allowed to cool to room temperature. The reaction mixture was acidified with 15% aqueous HCl, producing a precipitate. The precipitate was filtered and washed with $H_2O$ and the dried product was analyzed by $^1H$ NMR. Percent conversion of DBTA (II) for each ligand is presented in Table 2. Selectivities for DHTA (I) and the intermediate 2-bromo-5-dihydroxyterephalic acid (VII) are also presented in Table 2. Using either a methyl-bearing tertiary tetraamine (Ligand O, Comparative Example A) or no ligand (Comparative Example B) resulted in lower conversion than using the ligands of the working examples.

TABLE 2

[Structure I: 2,5-dihydroxyterephthalic acid]

[Structure II: 2,5-dibromoterephthalic acid]

[Structure VII: 2-bromo-5-hydroxyterephthalic acid]

| Ligand Code | Example | CONV (II, %) | SEL (VII, %) | SEL (I, %) | Ligand Structure |
|---|---|---|---|---|---|
| A | 3 | >99 | <1 | 84 | NMe₂—⁀—NH₂ |
| B | 4 | >99 | <1 | 94 | EtHN—⁀—NHEt |
| C | 5 | 92 | 5% | 12 | MeHN—(⁀)₅—NHMe |

TABLE 2-continued

I: 2,5-dihydroxyterephthalic acid

II: 2,5-dibromoterephthalic acid

VII: 2-bromo-5-hydroxyterephthalic acid

| Ligand Code | Example | CONV (II, %) | SEL (VII, %) | SEL (I, %) | Ligand Structure |
|---|---|---|---|---|---|
| D | 6 | >99 | <1 | 90 | Et$_2$N-CH$_2$CH$_2$-NHMe |
| E | 7 | 98 | 4 | 12 | 1,2-diaminobenzene |
| F | 8 | >99 | <1 | >98 | rac-trans-N,N'-dimethyl-1,2-diaminocyclohexane |
| G | 9 | >99 | <1 | 82 | MeHN-CH$_2$CH$_2$-NH$_2$ |
| H | 10 | 83 | 9 | 10 | 1,2-bis(4-pyridyl)ethane |
| I | 11 | >99 | <1 | 55 | Me$_2$N-CH$_2$CH$_2$-NMe$_2$ |
| J | 12 | >99 | <1 | 76 | 1,2-diaminocyclohexane |
| K | 13 | >99 | <1 | 96 | MeHN-CH$_2$CH$_2$-NHMe |

TABLE 2-continued
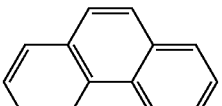
I
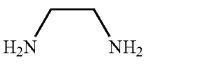
II
VII
| Ligand Code | Example | CONV (II, %) | SEL (VII, %) | SEL (I, %) | Ligand Structure |
|---|---|---|---|---|---|
| L | 14 | >99 | <1 | 11 | 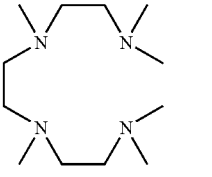 |
| M | 15 | >99 | 2 | 58 | $H_2N$~~~$NH_2$ |
| N | 16 | >99 | 3 | 49 | (i-Pr)HN~~~NH(i-Pr) |
| O | A (Comparative) | 64 | 17 | 11 | 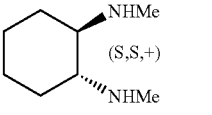 |
| P | 17 | >99 | <1 | 99 | 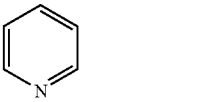 |
| Q | 18 | >99 | <1 | 88 | pyridine |
| R | 19 | >99 | <1 | 75 | 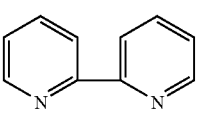 |
| — | B (Comparative) | 31 | 32 | 2 | No ligand (Comparative) |

Examples 20-23

Eight 2 mL reaction vials were each charged with 25 mg (0.077 mmol) of 2,5-dibromoterephthalic acid, followed by various amounts of 0.5 M aqueous sodium carbonate solution as shown in Table 3. Each of the mixtures was then treated with 0.003 mL of 0.23 M copper(I) bromide in acetonitrile and 0.003 mL of 0.5 M rac-trans-N,N'-dimethylcyclohexane-1,2-diamine (Ligand F). The reaction vials were closed and loaded into an 8-well reactor. The reactor was then sealed. About 12 psi (83 kPa) of $N_2$ pressure was applied. The reactor was heated to 90° C. and held at that temperature for 5 hours, then allowed to cool to room temperature. The reaction mixture was then acidified with 15% aqueous HCl, producing a light green precipitate. The precipitate was filtered, washed with water, dried, and analyzed by $^1$H NMR in DMSO-d6. Results are presented in Table 3.

TABLE 3

| Example | Amount $Na_2CO_3$ [in equivalents of $Na^+$] | % yield * by $^1$H NMR |
|---|---|---|
| 20 | 4.1 | 97 |
| 21 | 4.2 | 99 |
| 22 | 4.5 | 99 |
| 23 | 5 | 99 |

* Average of two values

Examples 24-29

These examples demonstrate the formation of 2,5-dihydroxyterephthalic acid from 2,5-dibromoterephthalic acid using different copper compounds and rac-trans-N,N'-dimethylcyclohexane-1,2-diamine (Ligand F). Under nitrogen, a predetermined amount of 2,5-dibromoterephthalic acid (set forth in Table 4) was combined with about the five times the weight $H_2O$, and a predetermined amount of $Na_2CO_3$ (set forth in Table 4) was then added. The mixture was heated to reflux with stirring for 30 min, remaining under a nitrogen atmosphere. Separately a predetermined amount of the copper compound (set forth in Table 4) and of rac-trans-N,N'-dimethylcyclohexane-1,2-diamine (Ligand F) were combined with 2 mL $H_2O$ under exclusion of air. For CuBr and CuCl the resulting mixture was subsequently stirred under an air atmosphere for about 30 seconds until the copper salt was dissolved before it was added to the reaction mixture. For $CuBr_2$, $CuSO_4$, Cu(OTf) (Toluene) and $Cu(OTf)_2$, the resulting catalyst solutions were added to the stirred reaction mixture via syringe at 80° C. under exclusion of air and stirred at 80° C. Samples were taken periodically to follow the conversion to DHTA. Table 4 gives the results as derived by $^1$H NMR spectroscopy. Times given indicate the approximate reaction time to reach the given conversion of starting material II.

TABLE 4

| Example | Cu source | Cu amount (mmol) | Ligand amount (mmol) | DBTA amount (mmol) | $Na_2CO_3$ amount (mmol) | Air | Time [h] | SEL [%] | CONV [%] |
|---|---|---|---|---|---|---|---|---|---|
| 24 | CuBr | 0.02 | 0.04 | 2 | 5 | Yes | ~1 | >99 | >99 |
| 25 | $CuBr_2$ | 0.02 | 0.04 | 2 | 5 | No | ~1 | >99 | >99 |
| 26 | CuOTf | 0.005 | 0.01 | 0.5 | 1.25 | No | 2.5 | 98 | 99 |
| 27 | $Cu(OTf)_2$ | 0.02 | 0.04 | 2 | 5 | No | ~1 | >99 | >99 |
| 28 | CuCl | 0.02 | 0.04 | 2 | 5 | Yes | 8.5 | 98 | 99 |
| 29 | $CuSO_4$ | 0.02 | 0.04 | 2 | 5 | No | ~1 | >99 | >99 |

Example 30

This example demonstrates the formation of 2,5-dihydroxyterephthalic acid from 2,5-dichloroterephthalic acid using CuBr and rac-trans-N,N'-dimethylcyclohexane-1,2-diamine (Ligand F). Under nitrogen, 2.00 g (8.51 mmol) of 2,5-dichloroterephthalic acid was combined with 10 g of $H_2O$. 0.938 g (8.85 mmol) of $Na_2CO_3$ was then added. The mixture was heated to reflux with stirring for 30 min, remaining under a nitrogen atmosphere. Another 1.31 g (12.34 mmol) of $Na_2CO_3$ was added to the reaction mixture and reflux was continued for 30 min. Separately, 12 mg of CuBr and 24 mg of rac-trans-N,N'-dimethylcyclohexane-1,2-diamine (Ligand F) were combined with 2 mL $H_2O$ under nitrogen. The resulting mixture was stirred under an air atmosphere until the CuBr was dissolved to give a deep purple solution. This solution was added to the stirred reaction mixture via syringe at 80° C. under nitrogen and stirred for 20 h at 80° C. After cooling to 25° C., the reaction mixture was acidified with HCl (conc.), producing a dark yellow precipitate. The yellow precipitate was filtered and washed with water. After drying, a total of 1.59 g (8.03 mmol, 94% yield) 2,5-dihydroxyterephthalic acid was collected. The purity was determined by $^1$H NMR to be >95%.

Where an embodiment of this invention is stated or described as comprising, including, containing, having, being composed of or being constituted by certain features, it is to be understood, unless the statement or description explicitly provides to the contrary, that one or more features in addition to those explicitly stated or described may be present in the embodiment. An alternative embodiment of this invention, however, may be stated or described as consisting essentially of certain features, in which embodiment features that would materially alter the principle of operation or the distinguishing characteristics of the embodiment are not present therein. A further alternative embodiment of this invention may be stated or described as consisting of certain features, in which embodiment, or in insubstantial variations thereof, only the features specifically stated or described are present.

Where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

Where a range of numerical values is recited herein, unless otherwise stated, the range is intended to include the endpoints thereof, and all integers and fractions within the range.

It is not intended that the scope of the invention be limited to the specific values recited when defining a range.

What is claimed is:

1. A process for preparing a 2,5-dialkoxyterephthalic acid comprising the steps of:
    (a) contacting a 2,5-dihaloterephthalic acid, as described generally by Formula III

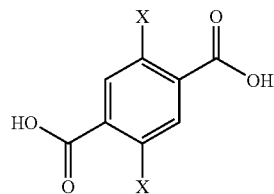

wherein X=Cl, Br, or I, with base in water to form therefrom the corresponding dibasic salt of the 2,5-dihaloterephthalic acid;
    (b) contacting the dibasic salt of the 2,5-dihaloterephthalic acid with base in water, and with a copper source in the presence of an amine ligand that coordinates to copper, to form the dibasic salt of 2,5-dihydroxyterephthalic acid from the dibasic salt of 2,5-dihaloterephthalic acid at a solution pH of at least about 8; wherein the ligand comprises, when it is a tetraamine, at least one primary or secondary amino group;
    (c) optionally, separating the dibasic salt of 2,5-dihydroxyterephthalic acid from the reaction mixture in which it is formed;
    (d) contacting the dibasic salt of 2,5-dihydroxyterephthalic acid with acid to form therefrom 2,5-dihydroxyterephthalic acid; and
    (e) converting the 2,5-dihydroxyterephthalic acid to a 2,5-dialkoxyterephthalic acid.

2. A process according to claim 1 wherein the 2,5-dihydroxyterephthalic acid is contacted under basic conditions with a dialkyl sulfate of the formula $R^9R^{10}SO_4$ wherein $R^9$ and $R^{10}$ are each independently a substituted or unsubstituted $C_{1-10}$ alkyl group.

3. A process for preparing a compound, monomer, oligomer or polymer from a 2,5-dihydroxyterephthalic acid comprising the steps of:
    (a) contacting a 2,5-dihaloterephthalic acid, as described generally by Formula III

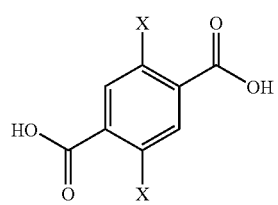

wherein X=Cl, Br, or I, with base in water to form therefrom the corresponding dibasic salt of the 2,5-dihaloterephthalic acid;
    (b) contacting the dibasic salt of the 2,5-dihaloterephthalic acid with base in water, and with a copper source in the presence of an amine ligand that coordinates to copper, to form the dibasic salt of 2,5-dihydroxyterephthalic acid from the dibasic salt of 2,5-dihaloterephthalic acid at a solution pH of at least about 8; wherein the ligand comprises, when it is a tetraamine, at least one primary or secondary amino group;
    (c) optionally, separating the dibasic salt of 2,5-dihydroxyterephthalic acid from the reaction mixture in which it is formed;
    (d) contacting the dibasic salt of 2,5-dihydroxyterephthalic acid with acid to form therefrom 2,5-dihydroxyterephthalic acid; and
    (e) subjecting the 2,5-dihydroxyterephthalic acid to a reaction to prepare therefrom a compound, monomer, oligomer or polymer.

4. A process according to claim 3 wherein a polymer prepared comprises a pyridobisimidazole-2,6-diyl(2,5-dihydroxy-p-phenylene)polymer.

5. A process according to claim 1 further comprising a step of subjecting the 2,5-dialkoxyterephthalic acid to a reaction to prepare therefrom a compound, monomer, oligomer or polymer.

6. A process according to claim 1 wherein, in steps (a) and (b), a total of about 4 to about 5 normal equivalents of water-soluble base are added to the reaction mixture per equivalent of 2,5-dihaloterephthalic acid.

7. A process according to claim 1 wherein the copper source comprises Cu(O), a Cu(I) salt, a Cu(II) salt, or a mixture thereof.

8. A process according to claim 1 where the ligand comprises a monoamine, diamine, triamine or a tetraamine.

9. A process according to claim 1 where the ligand comprises an N,N'-substituted diamine.

10. A process according to claim 1 wherein the ligand comprises a cyclic amine.

11. A process according to claim 1 wherein copper is provided in an amount of between about 0.1 and about 5 mol % based on moles of 2,5-dihaloterephthalic acid.

12. A process according to claim 1 wherein the ligand is provided in an amount of between about one and about two molar equivalents per mole of copper.

13. A process according to claim 3 wherein, in steps (a) and (b), a total of about 4 to about 5 normal equivalents of water-soluble base are added to the reaction mixture per equivalent of 2,5-dihaloterephthalic acid.

14. A process according to claim 3 wherein the copper source comprises Cu(O), a Cu(I) salt, a Cu(II) salt, or a mixture thereof.

15. A process according to claim 3 where the ligand comprises a monoamine, diamine, triamine or a tetraamine.

16. A process according to claim 3 where the ligand comprises an N,N'-substituted diamine.

17. A process according to claim 3 wherein the ligand comprises a cyclohexyl diamine.

18. A process according to claim 3 wherein the ligand comprises a cyclic amine.

19. A process according to claim 3 wherein copper is provided in an amount of between about 0.1 and about 5 mol % based on moles of 2,5-dihaloterephthalic acid.

20. A process according to claim 3 wherein the ligand is provided in an amount of between about one and about two molar equivalents per mole of copper.

* * * * *